United States Patent [19]

Polis, deceased et al.

[11] 4,245,111

[45] Jan. 13, 1981

[54] METHOD OF PREPARING PROSTAGLANDIN B₁ DERIVATIVES

[75] Inventors: B. David Polis, deceased, late of Wyndmoor, Pa., by Edith Polis, executrix; Sara F. Kwong, New Britan, Pa.

[73] Assignee: The United States of America as represented by the Secretary of the Navy, Washington, D.C.

[21] Appl. No.: 25,819

[22] Filed: Apr. 2, 1979

[51] Int. Cl.² ............................................. C07C 177/00
[52] U.S. Cl. ................................... 560/121; 562/503
[58] Field of Search ........................ 562/503; 560/121

[56] References Cited

U.S. PATENT DOCUMENTS 4,153,808  5/1979  Polis et al. ........................... 562/503

OTHER PUBLICATIONS

Polis, Fourth International Prostaglandin Conference, May 27, 1979.

*Primary Examiner*—Robert Gerstl
*Attorney, Agent, or Firm*—R. S. Sciascia; Henry Hansen

[57] ABSTRACT

An improved method for synthesizing and purifying $PGB_x$, a mixture of polymers of prostaglandin $B_1$. $PGB_x$ activity is assayed by measuring the minimum amount of $PGB_x$ required to restore complete phosphorylation ability to isolated rat liver mitochondria, first aged and degraded to the point where they exhibit less than 5% of the phosphorylating ability of normal mitochondria. A higher and more reproducible yield of $PGB_x$ of improved quality have been produced thereby.

10 Claims, 3 Drawing Figures

METHOD OF PREPARING PROSTAGLANDIN B₁ DERIVATIVES

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to prostaglandin B₁ derivatives, and more particularly to methods of preparing the prostaglandin B₁ derivatives, $PGB_x$, having the ability of restoring oxidative phosphorylation in aged degraded mitochondria.

A new class of polymeric derivatives $PGB_x$ of prostaglandin B₁ ($PGB_1$), called $PGB_x$, and methods for preparation thereof are disclosed in U.S. Pat. Application Ser. No. 635,947 filed Nov. 28, 1975 by B. David Polis et al, now U.S. Pat. No. 4,153,808 issued May 8, 1979. The $PGB_x$ has the unique property of restoring the in vitro phosphorylating ability of degraded rat liver mitochrondria. Subsequent experiments have shown $PGB_x$ to have unique properties of reversing the degenerative effects of experimentally induced myocardial ischemia in monkeys and brain ischemia in rabbits. See Angelakos, E. T. et al, *Recovery of Monkeys from Cardiogenic Shock after Myocardial Infarction with Ventricular Fibrillation-Effects of $PGB_x$*, Naval Air Development Center Report NADC-77308-60A, NTIS Accession No. AD A051744 (April 1978); and Kolata, R. J., *The Effect of $PGB_x$ on Neurological Recovery from Cerebral Ischemia in Rabbits*, Masters Thesis, University of Pennsylvania Veterinary School (1977).

Methods of the prior art for synthesizing, purifying, and assaying $PGB_x$ usually require a relatively long refluxing or heating process, and produced a relatively low yield of $PGB_x$ per unit weight of precursor. For example, the minimum preparation time for the methods disclosed in Patent Application Ser. No. 635,947 supra is 22 hours with a precursor of 13-14 dehydro $PGB_1$. For the precursors of $PGB_1$ and 13-14 dehydro $PGB_1$, the yields of useful $PGB_x$ are 72% and 57%, respectively, and are of nonuniform biological activity.

SUMMARY OF THE INVENTION

Accordingly, it is an object of the present invention to provide an improved method for synthesizing, purifying, and assaying polymeric derivatives $PGB_x$ from 15-keto prostaglandin B₁ methyl ester which will significantly reduce the preparation time while achieving higher yield, better quality, and more reproducibility. Another object of the invention is to provide a method of preparation which yields prostaglandin derivatives of the desired biological activity with substantially all impurities removed.

Briefly, these and other objects of the invention are accomplished by a novel method for synthesizing, purifying and assaying $PGB_x$. A starting material of 15-keto $PGB_1$ methyl ester is dissolved in ethanol and mixed in a solution of KOH. The mixture is heated until the light absorption maximum at a wavelength of 296 nm which is characteristic of 15-keto $PGB_1$ disappears, and the light absorption maximum at 243 nm appears which is indicative of the formation to $PGB_x$. The $PGB_x$ is then alternately rendered water-soluble and isobutanal-soluble for removing the impurities contained in the mixture. The isobutanol solution is finally evaporated leaving a residue of $PGB_x$. The residue is chromatographed and fractionated according to discrete time intervals and each fraction is assayed for its in vitro effect on mitochondrial oxidative phosphorylation. The activity is measured by the minimum amount of $PGB_x$ required to restore complete phosphorylation ability to isolated rat liver mitochondria, previously degraded by incubation at 28° C. to a level exhibiting less than 5% of the level found with nondegraded mitochondria.

For a better understanding of these and other objects and aspects of the invention, reference is made to the following detailed description taken in conjunction with the accompanying drawings wherein:

DESCRIPTION OF THE PREFERRED EMBODIMENT

The starting material, 15-keto $PGB_1$ methyl ester, is represented by the formula:

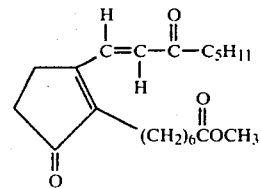

Trace amounts of $PGB_1$ occur in mammalian organisms and in certain species of coral. However, various synthetic methods for preparing it are known, but due to the lack of large scale synthetic laboratory facilities, synthesis of the starting material for the present invention is adapted from earlier smaller scale synthesis. See Polis, B. D. et al., *Studies on $PGB_x$ a Polymeric Derivative of Prostaglandin $B_1$: I-Synthesis and Purification of $PGB_x$*, Naval Air Development Center Report NADC-78235-60, (Oct. 30, 1978).

Five gram of 15-keto $PGB_1$ methyl ester is dissolved in 100 ml of ethanol and 100 ml of 2.0N KOH base solution is added. The resultant mixture is heated at 80° C. with the absorption characteristics of 15-keto $PGB_1$ and $PGB_x$ being monitored during the course of the reaction. The UV absorption maximum for 15-keto $PGB_1$ is 296 nm and the UV absorption maximum for $PGB_x$ is at 243 nm. The reaction, which takes approximately four hours, is completed when the $PGB_x$ activity reaches a maximum as determined by the in vitro mitochondrial test for restoration of oxidative phosphorylation. During the course of the reaction, the base solution hydrolyzes the 15-keto $PGB_1$ methyl ester to the salt form. The mixture is then cooled and shaken with equal parts of water and isobutanol, and acidified to pH 3.0 with 2.3N $HClO_4$, which has the unique advantage of converting the $PGB_x$ into a free acid soluble in isobutanol and converting the potassium to a relatively insoluble potassium perchlorate salt in water.

The mixture is then allowed to settle into separate isobutanol and water layers. The water and impurities therein are removed and the remaining isobutanol layer containing active $PGB_x$ is washed and separated twice with 100 ml of water.

The $PGB_x$ in the isobutanol layer is then shaken with 100 ml of 0.1M $NaHCO_3$ which converts the $PGB_x$ to a water-soluble salt form. The aqueous $NaHCO_3$ layer containing $PGB_x$, and the isobutanol and impurities dissolved therein, settle into separate layers and the isobutanol layer removed. The remaining $NaHCO_3$ layer containing $PGB_x$ is acidified to pH 3.0 with an acid, such as 1.0N HCl, to convert the $PGB_x$ back to its isobutanol-soluble acid form, insoluble in water and shaken with 100 ml of isobutanol. The water and other impurities therein are then removed, and the remaining isobutanol is first washed with 100 ml $H_2O$, two times, to remove excess acid, and then evaporated under reduced pressure to to leave a residue of approximately 4 g (80% yield) of crude $PGB_x$.

Figure 1:
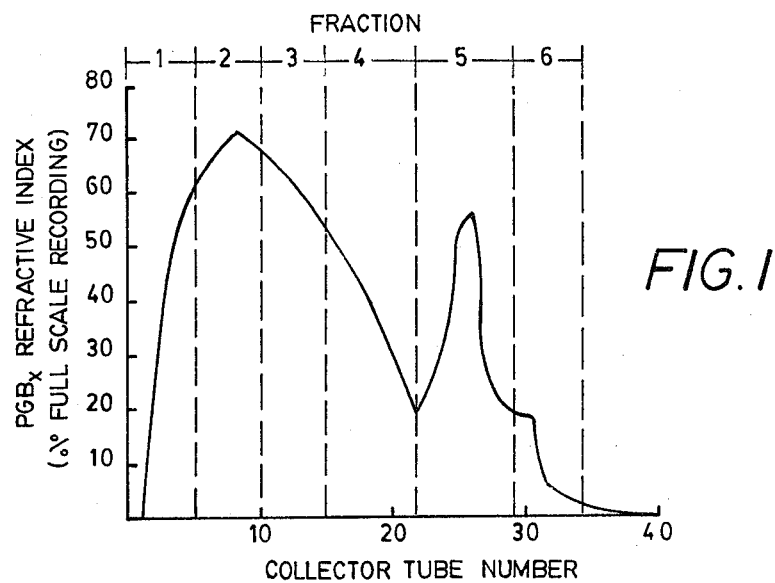
FIG. 1 represents a typical chromatogram for $PGB_x$.

The crude $PGB_x$ is then separated by molecular exclusion chromotography into fractions by monitoring the column effluent with a refractive index detector. Best results from the standpoint of increased purification and recovery of $PGB_x$ were obtained with methanol as the carrier solvent and a gel filtration packing, such as Sephadex LH20 manufactured by Pharmacia, Inc. Charges of 2 g of 20% $PGB_x$ in methanol are injected on a 95 cm×5 cm column of the adsorbent and chromatography is carried out at a flow rate of 20 ml per minute. Fractions are collected at one minute intervals with the course of chromatographic separation monitored by a refractive index detector. FIG. 1 represents the chromatogram for $PGB_x$ in methanol collected in forty tubes of discrete fractions. The fractions in tubes of selected refractive indices are combined to form six fractions which are dried and assayed for in vitro mitochondrial $PGB_x$ activity. Although $PGB_x$ is distributed in most of the fractions, highest activity of $PGB_x$ appears in fraction 2. The molecular weight range in this fraction is usually between 2200 and 2500, or approximately 6–7 monomeric units. The purification of $PGB_x$ resulting from one chromatography is shown in Table I below:

pH 7.35. The livers are homogenized (glass barrel, Teflon pestle) in the same solution and the mitochondria separated by differential centrifugation. The nuclei are sedimented at 1000 G for 15 minutes. The yield of mitochondria is increased by rehomogenizing the nuclei in three volumes of sucrose-EDTA and centrifuging at 1000 G. The 1000 G supernatant layers are combined and centrifuged at 10,000 G for 15 minutes to sediment the mitochondria. The mitochondrial pellet is homogenized in sucrose-EDTA and centrifuged at 6000 G, rehomogenized in fresh sucrose-EDTA and centrifuged at 4000 G. The supernatant layers from both the 10,000 G and 6000 G centrifugations are removed by aspiration while the 4000 g supernatant layer was "poured hard" to remove the "fluffy layer." To increase the yield of mitochondria, the "fluffy layer" is homogenized with two volumes of sucrose-EDTA and centrifuged at 6000 G. The 6000 G supernatant layer is "poured hard" and the pellets from both the 4000 G and 6000 G centrifugations are homogenized in sucrose-EDTA and centrifuged at 600 G to separate any cellular debris or nuclei that might still remain. After determining the protein content by the Biuret method, disclosed in Kingsley, G. R., Journal of Laboratory Chemical Medicine, Vol. 27, p. 840 (1942), the mitochondrial suspension is diluted with coldsucrose-EDTA to make a final concentration of 100 mg protein per ml. Usually 1.3 g of mitochondria are isolated from a 100 g of rat liver. The mitochondria are then stored at 4° C.

Prior to assaying the $PGB_x$, the mitochondria are further degraded by incubation at 28° C. in the absence of the phosphate acceptor ADP (adenosine diphosphate). Since the degree of degradation required for the $PGB_x$ effect varied with each mitochondrial preparation as well as the time of storage, preliminary incubations of varying times are run to determine the optimum degree of degradation. For this purpose, an aliquot of aged mitochondria (usually of the amount needed for one day's use) is diluted with cold distilled water and centrifuged to 6000 G. The supernatant is removed and an equivalent volume of 0.15 M sucrose plus $2.5 \times 10^{-4}$M EDTA is added, and the mitochondria suspended by gentle mechanical mixing. The optimal degradation time is determined by adding 4 mg of mito-

TABLE I

| Fraction | Molecular Weight | Weight | | $PGB_x$ Activity | | |
|---|---|---|---|---|---|---|
| | | Mg per Fraction | % Recovery | Units/Mg | Mg per Fraction | % Recovery |
| Starting | | 4190 | | 0.86 | 3603 | |
| 1 | 4300 | 500 | 12.0 | 0.89 | 445 | 12.4 |
| 2 | 2200–2500 | 1490 | 35.6 | 1.00 | 1490 | 41.4 |
| 3 | 1300 | 990 | 23.7 | 0.64 | 634 | 17.6 |
| 4 | 800 | 490 | 11.7 | 0.11 | 54 | 1.5 |
| 5 | 350 | 100 | 2.5 | 0.05 | 5 | 0.1 |
| 6 | — | 10 | 0.3 | — | — | — |

The $PGB_x$ activation of oxidative phosphorylation of degraded mitochondria disclosed in the Patent Application Ser. No. 635,947 supra employs the Warburg technique. $PGB_x$ activation in the present application is demonstrated as follows.

Mitochondria are isolated by a modification of the method disclosed by Hogeboom, G. H. et al., *Cytochemical Studies of Mammalian Tissues I. Isolation of Intact Mitochondria from Rat Liver*, Journal of Biological Chemistry, Vol. 172, page 619 (1948). Rats are decapitated, and their livers excised as rapidly as possible and washed with 0.3M sucrose (enzyme grade) containing $5 \times 10^{-4}$M EDTA (ethylene diamine tetra-acetic acid), chondria each into four beakers containing 0.1 ml of 0.1M phosphate buffer of pH 7.35, 0.15 ml of 0.2M alphaketoglutarate (pH 7.35), 0.1 ml of 0.1M $MgSO_4$ and water to a total volume of 2.01 ml. The beakers are covered and shaken at 28° C. for 5, 10, 15 and 20 minutes, respectively. At the end of each time period, 0.15 ml of a mixture containing 0.0333M ADP, 0.0333M AMP (adenosine monophosphate) and 0.66M KCl is added followed immediately with 0.04 ml of 3.75% bovine syrum albumin to give a final volume of 2.2 ml.

The order of addition and the composition of the reactants are summarized in Table II below.

TABLE II

| ORDER OF ADDITION | MITOCHONDRIAL DEGRADING MEDIUM | REACTION MIXTURE |
|---|---|---|
| water | 1.55 ml | 1.55 ml |
| phosphate buffer pH 7.35 | 4.98 mM | 4.55 mM |
| α-ketoglutarate pH 7.35 | 14.93 mM | 13.64 mM |
| MgSO$_4$ | 4.98 mM | 4.55 mM |
| aged Mitochondria | 1.99 mg/ml | 1.82 mg/ml |
| sucrose* | 5.97 mM | 5.45 mM |
| EDTA | 0.010 mM | 0.009 mM |
| AMP | — | 2.27 mM |
| ADP | — | 2.27 mM |
| KCl | — | 45.45 mM |
| bovine serum albumin | — | 0.68 mg/ml |

*added with mitochondria

Figure 2:
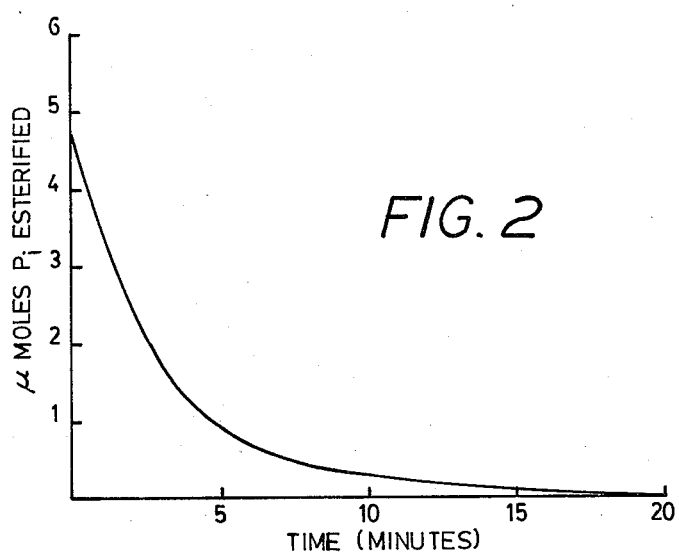
FIG. 2 represents a typical variation in oxidative phosphorylation of nondegraded aged mitochondria as a function of time of degradation at 28° C.

Shaking of the beakers is continued for 20 minutes at which time the reaction is terminated by the addition of 0.5 ml of 31% HClO$_4$. The inorganic phosphate concentration is then determined in the protein-free filtrate by the method disclosed in Dreisbach, R. H., *Submicrogram Determination of Inorganic Phosphate*, Analytical Biochemistry, Vol. 10, No. 169 (1965). That is, 0.5 ml aliquot of protein-free filtrate is added to 3.5 ml of water, 1 ml of 10% ammonium molybdate in 5N H$_2$SO$_4$ and 5 ml isobutanol. The mixture is shaken thoroughly and the phases allowed to separate. 0.5 ml of the isobutanol layer formed thereby is diluted to 5.0 ml with 3.2% H$_2$SO$_4$ in ethanol and the absorbane measured at 310 nm wavelength. The phosphate disappearance (or phosphate $P_i$ esterified) is calculated by the difference from the phosphate concentration found in each beaker at the end of the reaction time period to that in which no reaction has taken place, i.e., a reaction beaker in which perchloric acid is added prior to the addition of the mitochondria. The degradation time used to show the PGB$_x$ effect is chosen as the minimum time required to reduce the level of phosphorylation to less than 5% of the level shown in FIG. 2 for nondegraded mitochondria.

Figure 3:
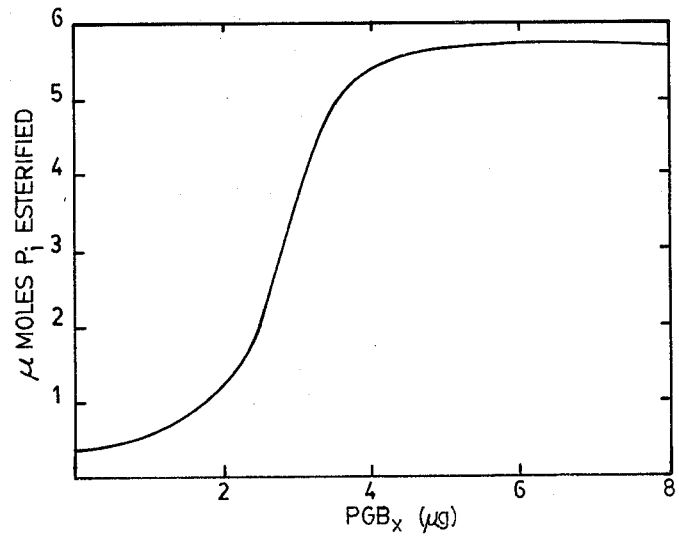
FIG. 3 represents a typical $PGB_x$ effect in restoring oxidative phosphorylation of degraded aged mitochondria.

Thus, having established the condition for mitochondrial degeneration to near zero phosphorylation, the PGB$_x$ effect is shown in FIG. 3 by adding varying amounts of PGB$_x$, e.g., 2, 4, 6, 8 μg during the predetermined incubation period and prior to the addition of the phosphate acceptor.

It is apparent in FIG. 3 that, in the absence of PGB$_x$, the ability of degraded mitochondria to carry out oxidative phosphorylation is markedly inhibited. When PGB$_x$ is added in small increments, such as 0-2 μg, a recovery of the phosphorylation ability may be noted after a short induction period. At the level of 2-4 μg PGB$_x$, a sharp increase in phosphorylation occurs. Above 4 μg PGB$_x$, the mitochondria are saturated and phosphorylation levels off. For purposes of quantification, a unit of PGB$_x$ activity is defined as the inverse ratio of the amount (in μg) of PGB$_x$ required to restore 50% of the phosphorylation (3.0μ moles esterified phosphate) to that required by the standard PGB$_x$ preparation. For this purpose the best fitting curve of the rising portion of the PGB$_x$ concentration - activity curve is calculated by the method of linear regression to yield the value of the constants, $a_0$ and $a_1$ in the equation that describes the curve: $Y = a_0 + a_1 X$. By substituting 3 for Y and solving for X, the amount of PGB$_x$ required for 50% recovery of activity is obtained. The unit of PGB$_x$ activity is then defined as $$K_a = \frac{X\ PGB_x\ \text{standard}}{X\ PGB_x\ \text{unknown}}$$

The $K_a$ values calculated in this manner describe the activity of the various PGB$_x$ preparation as follows:

When $K_a = 1$, activity of unknown is equal to activity of standard, $K_a - 1$, activity of unknown less than standard, $K_a > 1$, activity of unknown more than standard.

In addition, if the total amount of PGB$_x$ (in mg) is multiplied by the $K_a$ value, the numerical figure obtained is essentially a measure of the total activity of the sample. In this manner the recovery of the activity may be followed during any fractionation procedure.

From the foregoing, some of the advantages and novel features of the invention should now be apparent. For example, an improved method of synthesizing prostaglandin derivatives PGB$_x$ from a starting material of 15-keto PGB$_1$ methyl ester is disclosed which substantially reduces processing time with a higher yield of more predictable reproducibility.

It will be understood, of course, that various changes in the details and steps, which have been herein described and illustrated in order to explain the nature of the invention, may be made by those skilled in the art within the principle and scope of the invention as expressed in the appended claims.

What is claimed is:

1. A method of preparing a class of prostaglandin derivatives PGB$_x$ for restoring oxidative phosphorylation in aged degraded mitochondria, comprising, in combination, the steps of:

mixing substantially equal volumes of a 5% solution 15-keto PGB$_1$ methyl ester in ethanol and of 2 N base solution to form a first mixture;

heating said first mixture about four hours at 80° C. to form a reaction product containing the derivatives PGB$_x$ miscible in water; and extracting the residue derivatives PGB$_x$ from said product.

2. A method according to claim 1 wherein:

said base solution consists essentially of 2N KOH in solution.

3. A method according to claim 1 or 2 wherein said extracting step comprises:

alternately rendering the derivatives PGB$_x$ water soluble and isobutanal soluble for removing the impurities contained in the reaction product.

4. A method according to claim 3 wherein said extracting step further comprises:

mixing said product with water, an organic solvent and an acid to form a second mixture containing PGB$_x$ dissolved in the solvent and immiscible in water;

separating said second mixture to form first layers of water and of PGB$_x$ in solvent;

mixing said first layer of PGB$_x$ in solvent with a bicarbonate solution to form a third mixture containing PGB$_x$ dissolved in the bicarbonate solution and miscible in water;

separating said third mixture to form second layers of PGB$_x$ in bicarbonate solution and of solvent;

mixing said second layer of PGB$_x$ in bicarbonate solution with an acid to form a fourth mixture containing water and $PGB_x$ dissolved in the solvent;

separating said fourth mixture to form third layers of water and of $PGB_x$ in solvent; and evaporating the solvent in said third layer of $PGB_x$ in solvent to form a residue of said derivatives $PGB_x$.

5. A method according to claim 4 wherein:

said second mixture contains equal parts of water and organic solvent, and sufficient acid for pH 3.0.

6. A method according to claim 5 wherein:

said second mixture consists essentially of said reaction product, water, isobutanol and 2.3N $HClO_4$, and acidified to about 3.0 pH.

7. A method according to claim 4 wherein:

said third mixture consists essentially of said first layer of $PGB_x$ in solvent and 20 ml 0.1M $NaHCO_3$ per gram of said 15-keto $PGB_1$ methyl ester.

8. A method according to claim 4 wherein:

said fourth mixture contains sufficient acid for pH 3.0.

9. A method according to claim 8 wherein:

said fourth mixture consists essentially of said second layer of $PGB_x$ in bicarbonate solution, isobutanol and 1.0N HCl, and acidified to pH 3.0.

10. A method of preparing a class of prostaglandin derivatives $PGB_x$ for restoring oxidative phosphorylation in aged degraded mitochondria, consisting essentially of the steps of:

mixing substantially equal volumes of 5% solution 15-keto $PGB_1$ methyl ester in ethanol and 2 N KOH base solution to form a first mixture;

heating said first mixture about four hours at 80° C. to form a reaction product containing the derivatives $PGB_x$ miscible in water;

mixing said product with equal parts of water and isobutanal and sufficient 2.3N $HClO_4$ to form a second mixture of about pH 3.0 containing water and $PGB_x$ dissolved in the isobutanal;

separating said $PGB_x$ in isobutanal from said water;

mixing said $PGB_x$ in isobutanal with a 20 ml 0.1M $NaHCO_3$ solution per gram of said 15-keto $PGB_1$ methyl ester to form a third mixture containing isobutanal and $PGB_x$ dissolved in $NaHCO_3$ solution;

separating said $PGB_x$ in $NaHCO_3$ solution from said isobutanal;

mixing said $PGB_x$ in $NaHCO_3$ solution with sufficient 1.0N HCl and 20 ml isobutanal per gram of 15-keto $PGB_1$ methyl ester to form a fourth mixture of about pH 3.0 containing water and $PGB_x$ dissolved in isobutanal;

separating said $PGB_x$ in isobutanal from said water; and evaporating said $PGB_x$ in isobutanol to form a residue of said derivatives $PGB_x$.

* * * * *

UNITED STATES PATENT AND TRADEMARK OFFICE
CERTIFICATE OF CORRECTION

PATENT NO. : 4,245,111
DATED : January 13, 1981
INVENTOR(S) : B. David Polis et al It is certified that error appears in the above-identified patent and that said Letters Patent are hereby corrected as shown below:

Title or cover page, item [75] Inventors, change

"B. David Polis, deceased, late of Wyndmoor, Pa. by Edith Polis, executrix; Sara F. Kwong, New Britain, Pa." to --B. David Polis, deceased, late of Wyndmoor, Pa., by Edith Polis, executrix; Edith Polis, Wyndmoor, Pa; Sara F. Kwong, New Britain, Pa.--

Signed and Sealed this

Seventeenth Day of November 1981

[SEAL]

Attest:

GERALD J. MOSSINGHOFF

Attesting Officer     Commissioner of Patents and Trademarks